(12) United States Patent
Cumbo

(10) Patent No.: US 8,663,242 B2
(45) Date of Patent: Mar. 4, 2014

(54) SURGICAL NEEDLE AND SUTURE USED THEREWITH

(76) Inventor: Peter Cumbo, Presles (FR)

( * ) Notice: Subject to any disclaimer, the term of this patent is extended or adjusted under 35 U.S.C. 154(b) by 1243 days.

(21) Appl. No.: 11/794,851

(22) PCT Filed: Jan. 9, 2006

(86) PCT No.: PCT/FR2006/050006
§ 371 (c)(1),
(2), (4) Date: Aug. 23, 2007

(87) PCT Pub. No.: WO2006/072754
PCT Pub. Date: Jul. 13, 2006

(65) Prior Publication Data
US 2008/0108957 A1    May 8, 2008

(30) Foreign Application Priority Data
Jan. 7, 2005    (FR) ...................... 05 50069

(51) Int. Cl.
*A61B 17/10*    (2006.01)
*A61B 17/06*    (2006.01)

(52) U.S. Cl.
USPC .......................................... 606/139; 606/223

(58) Field of Classification Search
USPC .......................... 606/139, 185, 202, 222–227
See application file for complete search history.

(56) References Cited

U.S. PATENT DOCUMENTS

| | | | |
|---|---|---|---|
| 3,892,240 A * | 7/1975 | Park ............................... | 606/225 |
| 4,274,565 A * | 6/1981 | Russell .......................... | 223/102 |
| 5,391,182 A | 2/1995 | Chin | |
| 5,507,755 A | 4/1996 | Gresl et al. | |
| 5,683,415 A * | 11/1997 | Brunken ........................ | 606/222 |
| 5,928,268 A * | 7/1999 | Butwell et al. ................ | 606/222 |
| 6,595,911 B2 * | 7/2003 | LoVuolo ......................... | 600/30 |
| 2005/0070959 A1 * | 3/2005 | Cichocki, Jr. ................. | 606/223 |
| 2005/0256535 A1 * | 11/2005 | Capurro ........................ | 606/185 |
| 2005/0256536 A1 | 11/2005 | Grundeman | |

FOREIGN PATENT DOCUMENTS

| | | | | |
|---|---|---|---|---|
| SU | 1438724 A1 | 11/1988 | | |
| WO | WO-2004/002326 A | 1/2004 | | |
| WO | WO2004002326 | * 1/2004 | ............ | A61B 17/06 |

* cited by examiner

*Primary Examiner* — Corrine M McDermott
*Assistant Examiner* — Christina Lauer
(74) *Attorney, Agent, or Firm* — IM IP Law PLLC; C. Andrew Im

(57) ABSTRACT

The invention essentially relates to a surgical needle (17) comprising a long hollow body (18) and two ends (19, 20). The body (18) comprises a ventral wall (21) and a dorsal wall (22) which are connected to one another. According to the invention, the dorsal wall (22) and the ventral wall (21) extend along the long axis of the needle (17). Each of the two ends (19, 20) comprises a hollow beveled tip (23, 24). The needle (17) also comprises a hole (25) which is provided in the dorsal wall (22) of the body (18) and a slit (26) which is provided in the ventral wall (21). In this way, a suture (30) can slide inside the hollow body (18) of the needle, the suture being retained in position by the knot (29) or means for stopping thereof. For said purpose, the smallest diameter (27) of the hole (25) is greater than the largest width (28) of the slit (26).

20 Claims, 4 Drawing Sheets

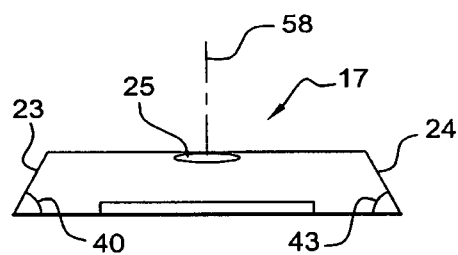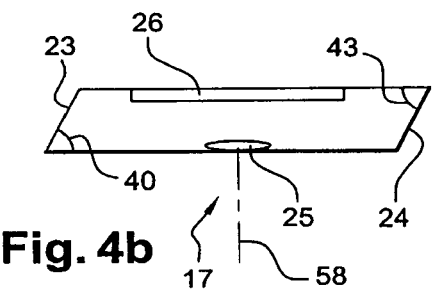
Fig. 4a    Fig. 4b
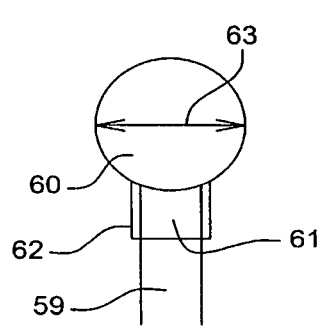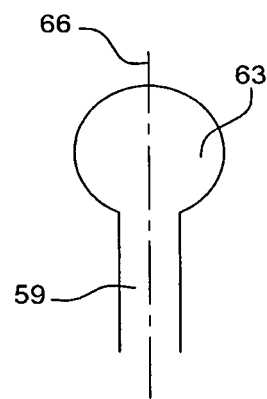
Fig. 5a    Fig. 5b

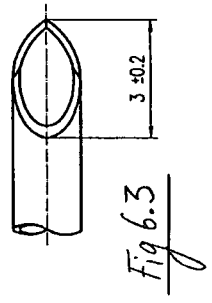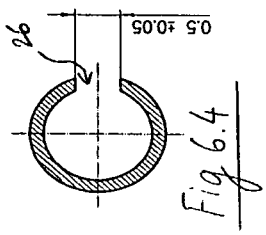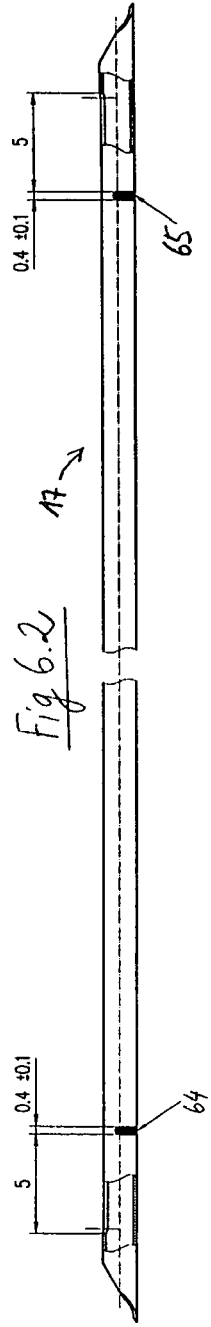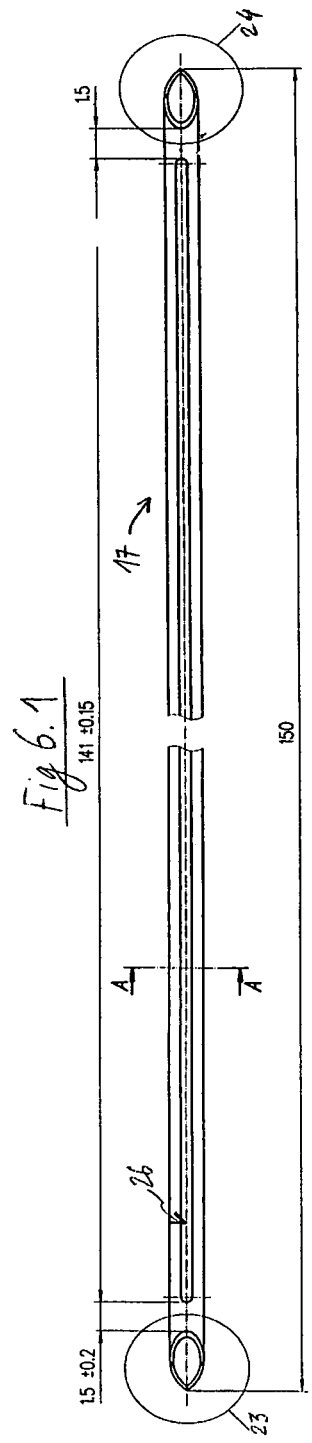

SURGICAL NEEDLE AND SUTURE USED THEREWITH

This application is a §371 from PCT/FR2006/050006 filed Jan. 9, 2006, which claims priority from FR 05 50069 filed Jan. 7, 2005, each of which is herein incorporated by reference in its entirety.

The present invention relates to a surgical needle and a suture for use with said needle. The main aim of the invention is to permit the movement of such a needle beneath the skin of a patient according to a trajectory determined by the operator, for example in a loop. The invention is particularly advantageous when applied in the field of plastic surgery, but it can also be used in other surgical practices. Demand for safe, simple procedures, that is to say those which present minimal side effects and time away from social activities, is on the increase, particularly in the field of cosmetic surgery.

Techniques already exist for using subcutaneous sutures aimed at restoring tautness in human tissue (of the face and body) of a patient whilst leaving no apparent, or at least minimal resulting scarring. However, these techniques are not always easy to implement and their results are not consistent.

In effect, it is normal practice to use sutures which have been specially designed to "hook" human tissue thanks to their "barbing". These are introduced under the skin using hollow, rectilinear catheters which only permit simple trajectories; a "round trip" trajectory is extremely difficult to perform.

Figure 1:
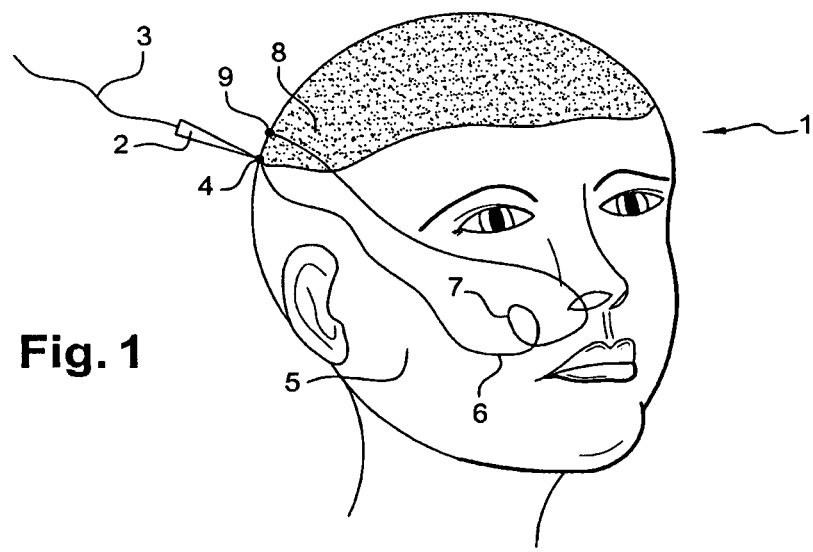

FIG. 1 shows a schematic representation of a patient 1 who's facial skin tissue is to be been re-tightened. The operation is in the nature of a type of non surgical facelift, leaving no visible scarring. It is carried out under straight local anaesthetic, does not require hospitalisation and is quickly performed.

In practice, in this example, in order to tighten tissue surrounding the cheekbone 5, a needle 2 pulling a suture 3 is introduced under the skin through an incision 4 in the temporal hair of the patient 1. This needle 2 describes a pre-established subcutaneous trajectory 6 which can have been drawn onto the patient's 1 face. This trajectory 6 is sinuous, including if necessary one or several loops 7 or other figures according to the desired result, and in particular according to the area of human tissue to be tightened. The trajectory 6 of the needle 2 is generally determined in such a way as to ensure that the needle 2 comes back out through the initial incision 4, or in an area close to this point.

Once the suture 3 has come back out, the two strands are pulled tight in order to obtain the desired effect and are knotted, possibly taking support from a solid structure such as the temporal fascia, well known to plastic surgeons. The resulting scarring, minimal, is situated under the hair line and therefore hidden. In some cases, a minimal resection of skin can be carried out in this zone.

Current processes employ a hollow cylindrical rectilinear catheter comprising a point at one end and a simple hole at the other and which serves as a guide for the introduction of the generally barbed suture. The catheter is introduced subcutaneously following the designated trajectory, then the point is brought to the surface the end point of the said trajectory and the suture passes downwards (by the point) into the body of the catheter in order to come back out at its point of entry. The catheter is then removed and the suture remains in place under the skin. All that remains is for this to be tightened once the tissue has been "picked-up" by the barbs of the suture. It is simple to imagine the limitations of such a technique.

Such types of catheters are able to describe rectilinear trajectories, such as curved or slightly sinuous trajectories. However, they do not permit, in particular, the description of a full loop in order to bring the end of the suture back out at a point close to its point of entry. It is difficult under these conditions to perform a real re-tightening of tissue with an anchorage that will ensure that it is maintained in place.

In effect, if the practitioner wishes to make a catheter follow such a trajectory, he/she will be obliged to break this said trajectory down into several stages, bringing to the surface the suture at each one, bearing in mind that the possibility of being able to reintroduce the suture by the same hole is largely improbable.

The invention described herewith proposes a solution to the problems previously described by permitting the threading of a suture through the tissue of the patient following any trajectory, without it ever coming to the surface before it has reached its final destination.

In order to do this, the needle which is the object of the invention is hollow, comprising two ends, each ending in a point, as well as a hole for introducing the suture and a longitudinal slit. The hole and the slit are situated on the opposite walls of the hollow body of the needle. The end of the employed suture is knotted or set with a sort of "weight" which has a diameter inferior to that of the hole of the needle in such a way that this permits its passage, but which has a diameter greater that the width of the slit which, as a result, retains the suture and allows it to be pulled by the needle.

Thereby the suture is introduced into the hole and, through the hole, into the slit by its free end (not set). Then the free end is pulled until the knot or the weight penetrates the hole and becomes blocked by the slit.

In this way, the suture is free to run along the length of the slit of the needle whilst remaining integral to it, and can follow trajectories as determined by the operator "on demand".

In effect, it is possible, at the moment where a change of direction is necessary, to partially bring the needle to the surface of the skin of the patient, by bringing out one of its points and part of its body, while keeping the other point and the thread buried under the skin. Then by executing a small lever movement and by rotating the needle, the needle can be redirected in the required direction and completely reinserted under the skin and so on and so forth by changing each time the directing point. The suture runs along the length of the slit and follows the needle without ever resurfacing.

Because the needle is hollow and sharp and because it is not necessary to bring the suture to the surface of the skin, even for describing the most sinuous trajectories, no unsightly scarring will be left by the needle. At the most, very temporary cutaneous perforations left by the needle can be observed as with any other subcutaneous injection carried out by a needle or a trocar. There is, therefore, no real scar, other than at the point of the initial incision, generally minimal and hidden.

The needle generally has a cylindrical rectilinear form. The points of the needle are beveled and sharp in order to permit good penetration of tissues.

A suture comprising a suture stop (type of "weight") or reinforcement at one of its ends can be supplied and used with the needle. This special suture presents a lower risk of weakening caused by friction against the length of the slit.

The employed suture can be absorbable or non absorbable, "barbed" or non barbed according to the choice and preferences of the practitioner.

The invention therefore relates to a surgical needle comprising:

a long hollow body and two ends; this body comprises a ventral wall and a dorsal wall which are connected to one another, the dorsal wall being geometrically opposite to the ventral wall, this dorsal wall and this ventral wall being in line with the line of the needle, the two hollow ends each having a point, characterised in that it further comprises:

a slit provided in the ventral wall, this slit extending between the two ends of the body.

The invention also relates to a suture employed with the surgical needle described herewith and characterised in that it comprises a suture stop of intermediary dimensions between the diameter of the hole of the needle and the greatest width of the ventral slit.

Figure 2:
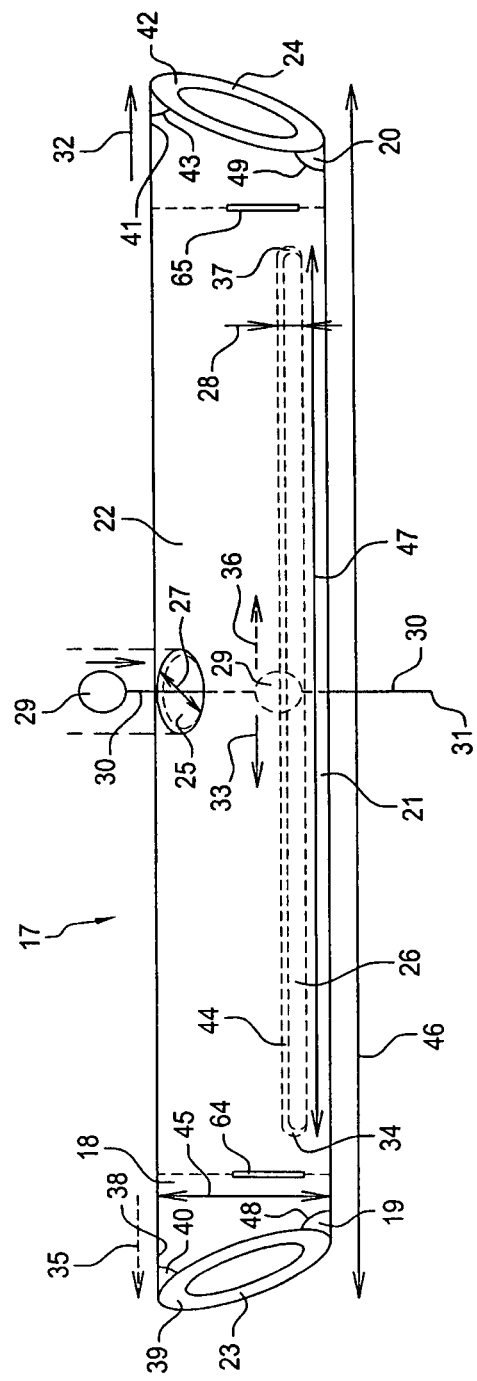

The invention will be more easily understood when reading the following description and studying the accompanying drawings. These figures are given as an indication of and are not limitative to the invention. These figures show:

FIG. 1 (already described): a schematic representation of a patient's face on which a re-tightening process is to be carried out;

FIG. 2: a schematic representation of a needle with two points according to the invention;

FIG. 3: a schematic representation of the various stages of a procedure using the needle according to the invention;

FIG. 4: schematic representations of the variations in design of the needle according to the invention;

FIG. 5: a schematic representation of a suture with a suture stop and of a variation having a bulge on one end and designed for use with the needle according to the invention, FIG. 6: Precise schematic representations of a needle according to the invention which does not include a hole.

FIG. 2 shows a surgical needle 17 according to the invention. This surgical needle 17 comprises a long or rectilinear hollow body 18 and two ends 19 and 20. This body 18 includes a ventral wall 21 and a dorsal wall 22 connected to one another. The dorsal wall 22 is geometrically opposite the ventral wall 21. This dorsal wall 22 and this ventral wall 21 extend in line with the line of the needle 17. Because the needle 17 is herewith cylindrical, this line corresponds with an axis of the needle. However, alternatively, the needle 17 can have a long form other than that of a cylinder, such as a curved form, in which the extension does not correspond with an axis.

The two ends 19 and 20 each comprise a hollow point 23 and 24. More precisely, the end 19 finishes in a point 23 and the end 20 in a point 24. The ending of the point 23, 24 situated at each end of the needle 17, most often constitutes the extension of the dorsal wall 22 of the said needle 17. However, the points 23 and 24 are not necessarily hollow vis-à-vis the invention. In effect, it is possible to create a needle which has solid points 23 and 24.

The needle 17 also comprises a hole 25 provided in the dorsal wall 22 of the body 18, and a slit 26 provided in the ventral wall 21. This slit 26 extends between the two ends 19 and 20 of the body 18 without, however, reaching their said extremities. This slit 26 is, therefore closed on each side in order to retain an ordinary surgical suture which slides through its centre. In one particular embodiment, a length of this slit 26 is superior to 10% of the length of the needle and/or superior to 5 times the diameter of the needle.

In addition, a smaller dimension of the hole 25 is greater than the largest width 28 of the slit 26. Because the hole 25 herewith is of a circular shape and the slit 26 is of a rectangular shape, the diameter 27 of the hole 25 is larger than the width of the slit 26. In a variation, the slit 26 is of an overall elliptical shape and the diameter 27 of the hole 25 is larger than the greatest width of this elliptical slit 26.

The dimensions of the hole 25 and of the slit 26 are thereby determined in such a way that the hole 25 allows for the passage of an obstruction 29, such as a knot or a thickness (bulge) or another means of stopping the suture 30, and for the slit to retain this obstacle 29. The slit 26 has thereby a width slightly superior to the diameter of the employed suture 30, but less than the diameter of the knot or suture stop 29. Furthermore, the length of the slit 26 is greater than the largest dimension of the hole.

To use the needle 17, an end 31 of the suture 30 is introduced into the interior of the hole 25 and of the slit 26. Once the knot 29 is positioned inside the needle 17, it is able to slide along the length of the slit 26 whilst being retained at each end of this slit 26 which is closed. Thereby, when the needle 17 moves in a rectilinear direction referenced 32 (directing end 20), the knot or suture stop 29 slide along the length of the slit 26 in the opposite direction 33 because the suture 30 will only be pulled by the needle 17 as of the moment when it butts up against the end 34 of the slit. The suture 30 will therefore be pulled by the needle 17 and follow its trajectory through the tissue.

Conversely, when the needle 17 moves in a direction 35 opposite from the direction 32 (directing end 19), the knot or suture stop 29 moves along the length of the slit 26 following a direction 36. When the knot or suture stop 29 comes up against the end 37 of the slit 26, it blocks and is thereby pulled with the suture 30 in the wake of the needle which describes the trajectory through the patients tissue desired by the operator. To this end; the ends 34 and 37 are generally perpendicular to the extension of the needle 17.

The body 18 of the needle 17 generally presents a cylindrical shape but variations are possible, such as a tronconic shape or a prescribed curve, which aim to optimise in particular the penetration of the needle 17 as well as its progression through tissue.

Each end 34, 37 of the slit 26 is distanced from the end 19, 20 as close as possible to a given length, generally in the order of one or several millimeters, or more according to the dimensions of the needle. The slit 26 is generally in a central and symmetrical position in one of the walls of the needle 17, generally the ventral wall 21.

The points 23, 24 situated at each end of the needle 17 are most often beveled, in such a way as that the ending of the points is along the extension of the dorsal wall 22 of the needle 17, that is to say that the bevel forms an acute angle 40, 43 with the dorsal wall 22 and an obtuse angle 48, 49 with the ventral wall 21. The dorsal wall 22 is in consequence longer than the ventral wall 21.

However, as is shown in FIG. 4, the bevels of the points 23, 24 can be angled in different ways. Alternatively, the points 32, 24 can take a different shape, such as a conical shape.

The body 18 comprises a diameter 45 in the order of millimeters and a length 46 of several cm, included for example between 5 and 20 cm. The diameter 27 of the hole 25 is in one example in the order of millimeters and is variable according to the dimensions of the needle 17. The slit 26 can stretch over a length 47 included between 4 and 15 cm. The slit 26 extends for example over a length 47 of less than 5 to 15 mm to that of the wall in which it is situated. In practice, the above mentioned dimensions depend on the type and diameter of the suture 30 employed as well as the type of intervention desired and of its locality (face or body . . . ).

The needle 17 can be made for example from a plate of steel of an adapted thickness and flexibility. This plate is to be rolled and its edges soldered in such a way as to obtain a cylindrical shape. More precisely, this plate can initially be machine finished in such a way as to create the hole 25 as well as the slit 26 previously described before being rolled. The beveled points can be created using the customary techniques for the manufacture of catheters and other needles and trocars. The points 23, 24 can for example be soldered to the ends 19 and 20 of the body 18. In another example, the needle 17 is created through casting. The hole 25 and the slit 26 can also be made after the creation of the body of the needle 18 and of its two points 23, 24. The needle 17 can also be embodied in an alternative material adapted to its use.

Given that the knot 29 slides evenly along the length of the slit 26, an edge 44 of the slit 26 situated in the thickness of the wall of the needle 17 can be machine finished, in such a way as to present a rounded or blunt shape which in consequence will not cut the suture. In one example, the edge 44 of the slit 26 is filed down in order to make it non cutting. Alternatively, the slit 26 can be coated with a non cutting material. In another variation, as can be seen in FIG. 5, it is the suture 30 which is reinforced around the part which is in contact with the edges of the slit 26.

A visual marker 64, 65 such as a notch or a line, coloured or not, can be inserted next to each end of the needle 17 in order to facilitate its use for the practitioner. This visual marker 64, 65 allows the practitioner to know the overall length of the needle 17 buried under the skin of the patient and to thus avoid pulling out the knot 29 during an operation. In effect, while the practitioner cannot see the marker of the part which is buried, he/she can pull on the needle 17 without pulling out the knot 29 from a skin tissue of the patient. To this effect, the marker 64, 65 generally extends perpendicularly to the extension of the needle 17. This marker 64, 65 can extend, in one example, over the entire circumference of the needle 17, or over a part of this circumference. In one embodiment, circular visual markers are created by laser at a distance from the ends of around 5 mm, and of a thickness of around 0.4 mm.

Alternatively, the needle 17 does not include a hole 25. In this variation, in order to put the suture in place, its free end is passed through one of the hollow points 23, 24 and then through the needle 17, and through the slit 26. This free end is then pulled until the other end of the suture, which carries a suture stop or a knot, comes up against the slit 26. Such a passage of the suture through a point and the slit is made possible by the fact that one end of the slit 26 is very close to that of a hollow point, the distance between them being in the order of 1 to 3 mm. Thereby, during the external manipulation of the needle, use of a lever effect for the rotation of the needle which is inside tissue is very successful.

FIG. 3 show a representation in stages of the employment of the needle 17 according to the invention.

Figure 3A:
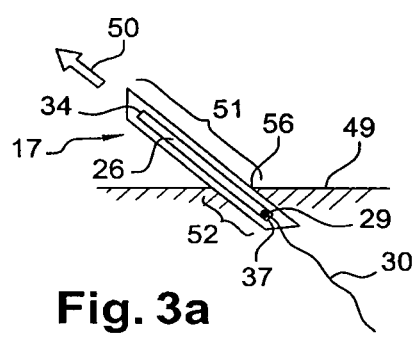

FIG. 3a shows a stage in which the needle 17, after having completed a part of the rectilinear or slightly curved subcutaneous trajectory perforates the skin 49 of a patient in a predetermined point 56 where it is necessary to change direction. More precisely, the needle 17 is driven to perforate the skin and then is partially brought to the surface by straight traction following the direction of the arrow 50 by the practitioner. This direction is generally the external extension of the path of the needle 17 through tissue. The needle 17 is thus pulled, in such a way as to ensure that the opposite end of the needle as well as the whole of the suture 30 (including the knot 29) remains inside the tissue 49 at all times. The visual marker 64, 65 (notch or line) close to each end of the needle 17 serves where necessary to guide the practitioner and thus enables him/her to avoid bringing the needle to the surface too often. A large part 51 of the needle remains therefore outside of the tissue 49, whereas a small part 52 of the needle 17, on the inside of which is the knot 29, remains inside the tissue 49. The knot 29 is at this moment blocked against the end 37 of the slit 26.

Figure 3B:
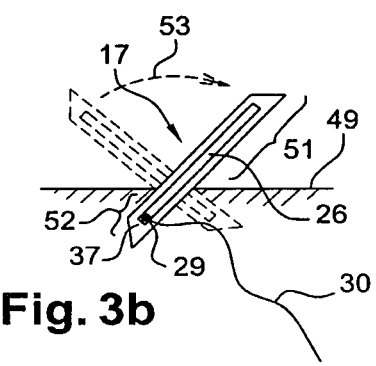

In the following stage represented in FIG. 3b, the practitioner employs a lever and rotation action on the large part 51 of the needle 17, in such a way as to pivot the whole needle 17 following an angle 53. This angle 53 is determined by the trajectory that the practitioner wishes the needle 17 to follow. Because the tissue 49 is generally supple and elastic, the practitioner has no difficulty in pointing the needle 17 in the desired direction.

After the rotation, the large part 51 of the needle remains outside of the tissue 49, whereas the smaller part 52, on the inside of which is the knot 29, remains inside the tissue 49. The knot 29 remains blocked against the end 37 of the slit 26.

Figure 3C:
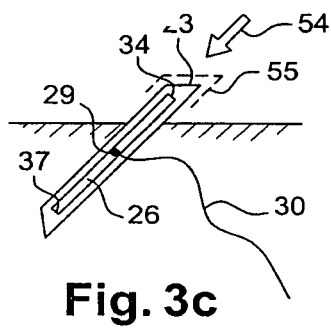

As is represented in FIG. 3c, once the direction of the needle 17 corresponds to that which is required, the practitioner can re-bury the needle 17 in the tissue following this direction schematised by the arrow 54. To avoid injuring him/herself when pushing the needle, the practitioner can use a cap 55 to cover the point 23 which is outside of the tissue 49. This cap 55 generally comprises a shape which is compatible with those of the points 23 and 24, so that using it will not present a risk of blunting them. In one example, the cap 55 is embodied in a plastic material.

When the needle 17 penetrates the tissue 49, it does not immediately pull the suture 30. In effect, initially, the knot or suture stop 29 slides along the length of the slit 26 without there having been any real movement of the suture 30 inside the tissue. Then, once the knot 29 arrives at and blocks against the opposite end 34 to the end 37 of the slit 26, the suture 30 is once again pulled by the needle 17. This suture 30 therefore follows once again the trajectory imposed by the needle 17.

Figure 3D:
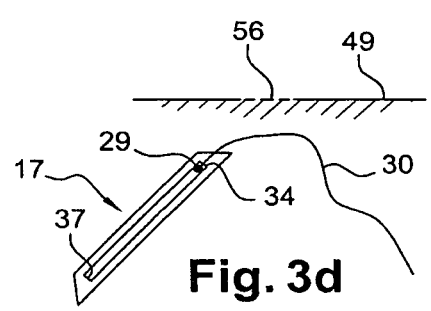

Thereby, as represented in FIG. 3d, the needle 17 can continue to guide the suture 30 along the practitioner's desired trajectory. The needle 17 can follow sinuous trajectories with any curve radii, without the need for the suture 30 to come out of the tissue layers 49. Furthermore, the punctures caused by the needle 17 during its successive passages through the cutaneous barrier leave very little trace after the intervention, healing perfectly in very little time in the same way as ordinary perfusions or injections.

FIG. 4 show schematic representations of variations to the embodiment of the needle 17.

On FIG. 4a, the needle 17 comprises the points 23, 24 which are symmetrically beveled according to a sagittal axis 58 and at the expense of the dorsal face 22. More precisely, the acute angles 40 and 43 of points 23 and 24 are situated on the same side as the slit 26.

On FIG. 4b, points 23 and 24 are asymmetrically beveled in relation to the axis 58. Thus, the acute angle 40 of point 23 is situated on the same side as the hole 25, whereas the acute angle 43 of point 24 is situated on the same side as the slit 26.

FIG. 5a shows a schematic representation of an example of the suture/suture stop which can be employed with the needle 17 according to the invention. This suture 59 comprises a suture stop 60 of a diameter 63 which is intermediary between the smallest dimension of the hole 25 and the greatest dimension of the width of the slit 26. More generally, where the suture stop 60 has a normal shape, it possesses the intermediary dimensions between the smallest dimension of the hole 25 and the greatest dimension of the width of the slit 26.

This suture stop 60 can be set with an end 61 of the suture 60. More precisely, a metal sleeve 62 linked to this suture stop 60 is crushed using a tool, such as a clip, in such a way as to compress the end 61 of the suture 59 and to block it. The suture stop 60 is embodied using a material, such as steel, which is resistant the effects of cutting.

FIG. 5b represents a suture, specially designed, which has a bulge 63 at one end which serves as a suture stop. This bulge 63 can for example be obtained using casting, by adding an extra quantity of material to one end of a suture mold designed for this purpose. This bulge 63 extends radially in relation to an axis 66 of the suture and can for example take the form of a ball.

Of course, the sutures employed in the invention can be of various different types, for example smooth or barbed. To help with the introduction of barbed sutures into the slit 26, it is possible to surround them with a smooth, flexible sheath. In this way, the barbs of the suture, which extend radially in relation to the axis of the suture and which impair the introduction of the suture, do not come into contact with the edge of the needle 17. The use of the sheath is particularly advantageous with a needle without a hole 25.

FIG. 6 show precise schematic representations of a needle 17 according to the invention without a hole. The specified dimensions on these figures are given in millimeters.

FIG. 6.1 shows an overhead view of the needle 17 represented on a scale of 5:1. FIG. 6.2 shows a side view of the needle 17. FIG. 6.3 shows a detailed view of the beveled points 23, 24 represented on a scale of 10:1. FIG. 6.4 shows a cross section A-A of the needle 17 on a scale of 20:1.1.

More precisely, in this embodiment, the needle 17 measures 150 mm and is in the form of a stainless steel tube of a diameter of 1.2 to 1.5 m. Whereas the slit 26, centred in relation to the needle, possesses a length of 141 mm and a width of 0.5 mm. This axial slit 26 is angled with the bevels at more or less 5 degrees.

Furthermore, the beveled points 23 and 24 are of an elliptical shape and extend along a length of around 3 mm. Points 23 and 24 each comprise a facetted bevel according to UN-1050 and are angled at more or less 5 degrees in relation to a wall of the needle 17. All these values are given with around a 10% tolerance.

Notches 64 and 65 are created by laser on half of the outline of the needle 17, being 180 degrees, at more or less 5 degrees. These notches possess in general the same angle as the bevels.

The invention claimed is:

1. A surgical needle and a suture, the surgical needle comprising:
   a long hollow body and two hollow ends, the body comprising a ventral wall and a dorsal wall connected to one another, the dorsal wall being geometrically opposite the ventral wall, the dorsal wall and the ventral wall being in line with the line of the needle, each hollow end comprising a point; and
   a closed slit provided in the ventral wall, extends between the two hollow ends of the hollow body, the slit lying in the direction of the length of the needle, a length of the slit being superior to 10% of the length of the needle;
   the suture comprising a stop at one end, the slit having a width greater than a diameter of the suture but less than a dimension of the stop; and wherein the suture being introduced into an interior of the slit such that the stop moves along the length of the slit while being retained at each end of the slit which is closed, the suture being pulled by the needle when an extremity of the suture comprising the stop butts against one of the ends of the slit, thereby permitting threading of the suture through the tissues of a patient following any trajectory, without the suture coming out of the surface before the suture has reached its final destination.

2. The surgical needle and the suture of claim 1, wherein the points of the hollow ends are hollow.

3. The surgical needle and the suture of claim 1, wherein the length of this slit is superior by 5 times to the diameter of the needle.

4. The surgical needle and the suture of claim 1, further comprising a hole provided in the dorsal wall of the hollow body.

5. The surgical needle and the suture of claim 4, wherein the length of the slit is greater than a largest dimension of the hole.

6. The surgical needle of claim 4, wherein the hole (1) has dimensions in the order of millimeters, variable according to the dimensions of the needle; or (2) is circular and has a diameter greater than a diameter of ordinary surgical sutures; or (3) has dimensions such that a smallest dimension of the hole is greater than a largest width of the slit.

7. The surgical needle and the suture of claim 4 capable of being used with a suture comprising a suture stop of dimensions which are intermediary between a smallest dimension of the hole and a greatest width of the slit.

8. The surgical needle and the suture of claim 7, wherein the suture stop includes a metallic sleeve which is set with one end of the suture.

9. The surgical needle and the suture of claim 7, wherein the suture further comprises a bulge in one end of the suture which serves as a suture stop, the bulge being obtained by casting.

10. The surgical needle and the suture of claim 1 wherein the slit is of an overall elliptical shape.

11. The surgical needle and the suture of claim 1 wherein each hollow end finish in a beveled point such that endings of the two hollow ends constitute the extension of one of the ventral and dorsal walls in a symmetrical manner.

12. The surgical needle and the suture of claim 11, further comprising a cap comprising a shape compatible with the beveled points and operable to cover one of the beveled points during manipulations.

13. The surgical needle and the suture of claim 1 wherein the body comprises a cylindrical shape.

14. The surgical needle and the suture of claim 1, wherein the body comprises a diameter in the order of millimeters and a length between 5 and 20 cm.

15. The surgical needle and the suture of claim 1, wherein the slit extends over a length of less than 5 to 15 mm to that of a wall in which the slit is situated.

16. The surgical needle and the suture of claim 1, wherein an edge of the slit which is situated in a thickness of the needle is rounded off or coated in a non-cutting material.

17. The surgical needle and the suture of claim 1, wherein the needle is made of steel.

18. The surgical needle and the suture of claim 1, further comprising a visual marker with at least one of the following: a colored or non-colored notch or a line, the visual marker being inserted close to each hollow end.

19. A surgical needle and a suture, the suture comprising a stop at one end and the surgical needle comprising:
   a long hollow body and two hollow ends, the body comprising a ventral wall and a dorsal wall connected to one another, the dorsal wall being geometrically opposite the ventral wall, the dorsal wall and the ventral wall being in line with the line of the needle, each hollow end comprising a point; and
   a closed slit provided in the ventral wall, extends between the two hollow ends of the hollow body, the slit lying in the direction of the length of the needle, a length of the slit being superior to 10% of the length of the needle; and wherein the slit having a width greater than a diameter of the suture but less than a dimension of the stop, and the stop moves along the length of the slit while being retained at each end of the slit which is closed, and the suture is pulled by the needle when an extremity of the suture comprising the stop butts against one of the ends of the slit.

20. A surgical needle and a suture, the surgical needle comprising:

a long hollow body and two hollow ends, the body comprising a ventral wall and a dorsal wall connected to one another, the dorsal wall being geometrically opposite the ventral wall, the dorsal wall and the ventral wall being in line with the line of the needle, each hollow end comprising a point; and a closed slit provided in the ventral wall, extends between the two hollow ends of the hollow body, the slit lying in the direction of the length of the needle, a length of the slit being superior to 10% of the length of the needle; and the suture comprising a stop at one end being introduced into an interior of the slit such that the stop moves along the length of the slit while being retained at each end of the slit which is closed, and the suture is pulled by the needle when an extremity of the suture comprising the stop butts against one of the ends of the slit, thereby permitting threading of the suture through the tissues of a patient following any trajectory, without the suture coming out of the surface before the suture has reached its final destination.

* * * * *